US011479826B2

(12) United States Patent
Grönewald et al.

(10) Patent No.: US 11,479,826 B2
(45) Date of Patent: Oct. 25, 2022

(54) NUCLEIC ACIDS AND METHODS FOR THE DETECTION OF *ENTEROBACTER SAKAZAKII* (*CRONOBACTER* SPP.)

(71) Applicant: BIOTECON DIAGNOSTICS GMBH, Potsdam (DE)

(72) Inventors: Cordt Grönewald, Berlin (DE); Kornelia Berghof-Jäger, Berlin (DE)

(73) Assignee: Biotecon Diagnostics GmbH, Potsdam (DE)

( * ) Notice: Subject to any disclaimer, the term of this patent is extended or adjusted under 35 U.S.C. 154(b) by 21 days.

(21) Appl. No.: 14/549,467

(22) Filed: Nov. 20, 2014

(65) Prior Publication Data

US 2015/0080258 A1 Mar. 19, 2015

Related U.S. Application Data

(63) Continuation of application No. 13/389,366, filed as application No. PCT/EP2010/004794 on Aug. 4, 2010, now abandoned.

(30) Foreign Application Priority Data

Aug. 7, 2009 (EP) .................... 09010239

(51) Int. Cl.
C12Q 1/689 (2018.01)
(52) U.S. Cl.
CPC ......... C12Q 1/689 (2013.01); *C12Q 2600/16* (2013.01); *Y02A 50/30* (2018.01)
(58) Field of Classification Search
CPC .................................................. C12Q 1/689
See application file for complete search history.

(56) References Cited

U.S. PATENT DOCUMENTS 7,202,027 B1 * 4/2007 Grabowski ............ C12Q 1/689
435/6.16

FOREIGN PATENT DOCUMENTS

WO WO 2004/104550 A2 12/2004
WO WO 2009/035955 A1 3/2009

OTHER PUBLICATIONS

Pisz et al. (2007) Differentiation of genes extracted from non-viable versus viable micro-organisms in environmental samples using ethidium monoazide bromide. Journal of Microbiological Methods, 71:312-318.*
CP000783.1 (NCBI accession sequence, GI:156530483, priority to Jan. 15, 2008, nucleotide positions 3981501-3981700, 4 pages).*
Nelson et al. "Lehninger Principles of Biochemistry, 4th ed". New York:W. H. Freeman and Company, 2005, p. 320.*
Mullane et al. (2008) Development of Multiple-Locus Variable-Number Tandem-Repeat Analysis for the Molecular Subtyping of Enterobacter sakazakii. Applied and Environmental Microbiology, 72(4):1223-1231.*
Buck et al. (1999) Design Strategies and Performance of Custom DNA Sequencing Primers. BioTechniques, 27:528-536.*
Kampfer et al. (2014) *Pseudocitrobacter* gen. nov., a novel genus of the Enterobacteriaceaewith two new species *Pseudocitrobacter faecalis* sp. nov., and *Pseudocitrobacter anthropi* sp. nov, isolated from fecal samples fromhospitalized patients in Pakistan. Systematic and Applied Microbiology, 37:17-22.*
Brady et al. (2013) Systematic and Applied Microbiology, 36:309-319.*
Stephan et al. (2014) International Journal of Systematic and Evolutionary Microbiology, 64:3402-3410.*
Rozen et al. (2000) PrimerS on the WWW for general users and for biologist programmers. In: Krawetz S, Misener S (eds) Bioinformatics Methods and Protocols: Methods in Molecular Biology. Humana Press, Totowa, NJ, pp. 365-389 (Year: 2000).*
Seo et al. (2005) Rapid, Specific Detection of Enterobacter sakazakii in Infant Formula Using a Real-Time PCR Assay. Journal of Food Protection, 68(1):59-63 (Year: 2005).*
Jaradat et al. (2009) Isolation of *Cronobacter* spp. from infant food, herbs and environmental samples and the subsequent identification and confirmation of the isolates using biochemical, chromogenic assays, PCR and 16S rRNA sequencing. BMC Microbiology, 9(225):pp. 1-11 (Year: 2009).*
Stephan et al. (2008) *Enterobacter pulveris* sp. nov., isolated from fruit powder, infant formula and an infant formula production environment. International Journal of Systematic and Evolutionary Microbiology, 58:237-241 (Year: 2008).*
Stephan et al. (2007) *Enterobacter turicensis* sp. nov. and *Enterobacter helveticus* sp. nov., isolated from fruit powder. International Journal of Systematic and Evolutionary Microbiology, 57:820-826 (Year: 2007).*
Database Geneseq (online), "B. stearothermophilus argC PCR primer argCfin-pHav2, SEQ ID No. 20," Database Accession No. ADQ25697 (Oct. 7, 2004).
Liu et al., "PCR and oligonucleotide array for detection of *Enterobacter sakazakii* in infant formula," *Molecular and Cellular Probes*, 20(1): 11-17 (2006).
Liu et al., "Real time PCR using TaqMan and SYBR Green for detection of *Enterobacter sakazakii* in infant formula," *Journal of Microbiological Methods*, 65(1): 21-31( 2006).
European Patent Office, International Search Report in International Patent Application No. PCT/EP2010/004794 (dated Oct. 20, 2010).
Chen et al, Bacteriological Analytical Manual, Chapter 29, Cronobacter, FDA Food Science Research Laboratory Methods, https://www.fda.gov/Food/FoodScienceResearch/LaboratorvMethods/ucm289378.htm (last accessed Jun. 16, 2017).

(Continued)

*Primary Examiner* — Neil P Hammell
(74) *Attorney, Agent, or Firm* — Leydig, Voit & Mayer, Ltd.

(57) ABSTRACT

Provided are detection means and method specific for the genus *Cronobacter* (*E. sakazakii*) which are sensitive by using a target molecule which is multiple existent in *Cronobacter* cells.

3 Claims, 5 Drawing Sheets
Specification includes a Sequence Listing.

(56) References Cited

OTHER PUBLICATIONS

Svobodová et al., "Novel Method for Reliable Identification of *Siccibacter* and *Franconibacter* Strains: from "Pseudo-Cronobacter" to New Enterobacteriaceae Genera", *Applied and Environmental Microbiology*, 83(13): 1-14 (2017).

* cited by examiner

*23S-ITS2-5S region including the hybridization positions of the oligonucleotides of this invention*

FIG. 2

Selective amplification of DNA from viable Cronobacter cells after treatment with EMA Enrichment cultures with $10^6$/ml viable or dead C. sakazakii cells were prepared with or without treatment with ethidium monoazide bromide (EMA). The resulting DNA extracts were tested with the multiplex real-time PCR for Cronobacter and Enterobacteriaceae detection.

SEQUENCE LISTING

```
<160> NUMBER OF SEQ ID NOS: 38

<210> SEQ ID NO 1
<211> LENGTH: 125
<212> TYPE: DNA
<213> ORGANISM: Synthliboramphus antiquus

<400> SEQUENCE: 1
ttaaccttac aacgccaaag aagtctggcg tgttgagaga caattcagct tgtgacggat    60
aracgttcat ggcggaagcg gtgracgrac agaatttgcc tggcggctgt agcgcggtgg   120
tccca                                                              125

<210> SEQ ID NO 2
<211> LENGTH: 22
<212> TYPE: DNA
<213> ORGANISM: Synthliboramphus antiquus

<400> SEQUENCE: 2
accttacaac gccaaagaag tc                                            22

<210> SEQ ID NO 3
<211> LENGTH: 16
```

```
<212> TYPE: DNA
<213> ORGANISM: Synthliboramphus antiquus

<400> SEQUENCE: 3
tgtagcgcgg tggtcc                                              16

<210> SEQ ID NO 4
<211> LENGTH: 29
<212> TYPE: DNA
<213> ORGANISM: Synthliboramphus antiquus

<400> SEQUENCE: 4
aagcggtgaa cggacagaat ttgcctggc                                29

<210> SEQ ID NO 5
<211> LENGTH: 29
<212> TYPE: DNA
<213> ORGANISM: Synthliboramphus antiquus

<400> SEQUENCE: 5
aagcggtgga cggacagaat ttgcctggc                                29

<210> SEQ ID NO 6
<211> LENGTH: 29
<212> TYPE: DNA
<213> ORGANISM: Synthliboramphus antiquus

<400> SEQUENCE: 6
aagcggtgaa cgaacagaat ttgcctggc                                29

<210> SEQ ID NO 7
<211> LENGTH: 29
<212> TYPE: DNA
<213> ORGANISM: Synthliboramphus antiquus

<400> SEQUENCE: 7
aagcggtgga cgaacagaat ttgcctggc                                29

<210> SEQ ID NO 8
<211> LENGTH: 31
<212> TYPE: DNA
<213> ORGANISM: Synthliboramphus antiquus

<400> SEQUENCE: 8
ttcagcttgt gacggataaa cgttcatggc g                             31

<210> SEQ ID NO 9
<211> LENGTH: 31
<212> TYPE: DNA
<213> ORGANISM: Synthliboramphus antiquus

<400> SEQUENCE: 9
ttcagcttgt gacggataga cgttcatggc g                             31

<210> SEQ ID NO 10
<211> LENGTH: 25
<212> TYPE: DNA
<213> ORGANISM: Synthliboramphus antiquus

<400> SEQUENCE: 10
gaagtctggc gtgttgagag acaat                                    25

<210> SEQ ID NO 11
```

```
<211> LENGTH: 31
<212> TYPE: DNA
<213> ORGANISM: Synthliboramphus antiquus

<400> SEQUENCE: 11
aaacgttcat ggcggaagcg gtgaacgaac a                              31

<210> SEQ ID NO 12
<211> LENGTH: 31
<212> TYPE: DNA
<213> ORGANISM: Synthliboramphus antiquus

<400> SEQUENCE: 12
agacgttcat ggcggaagcg gtgaacgaac a                              31

<210> SEQ ID NO 13
<211> LENGTH: 31
<212> TYPE: DNA
<213> ORGANISM: Synthliboramphus antiquus

<400> SEQUENCE: 13
agacgttcat ggcggaagcg gtggacgaac a                              31

<210> SEQ ID NO 14
<211> LENGTH: 31
<212> TYPE: DNA
<213> ORGANISM: Synthliboramphus antiquus

<400> SEQUENCE: 14
agacgttcat ggcggaagcg gtggacggac a                              31

<210> SEQ ID NO 15
<211> LENGTH: 31
<212> TYPE: DNA
<213> ORGANISM: Synthliboramphus antiquus

<400> SEQUENCE: 15
aaacgttcat ggcggaagcg gtggacgaac a                              31

<210> SEQ ID NO 16
<211> LENGTH: 31
<212> TYPE: DNA
<213> ORGANISM: Synthliboramphus antiquus

<400> SEQUENCE: 16
aaacgttcat ggcggaagcg gtgaacggac a                              31

<210> SEQ ID NO 17
<211> LENGTH: 31
<212> TYPE: DNA
<213> ORGANISM: Synthliboramphus antiquus

<400> SEQUENCE: 17
aaacgttcat ggcggaagcg gtggacggac a                              31

<210> SEQ ID NO 18
<211> LENGTH: 31
<212> TYPE: DNA
<213> ORGANISM: Synthliboramphus antiquus

<400> SEQUENCE: 18
agacgttcat ggcggaagcg gtgaacggac a                              31
```

```
<210> SEQ ID NO 19
<211> LENGTH: 125
<212> TYPE: DNA
<213> ORGANISM: Synthliboramphus antiquus

<400> SEQUENCE: 19
ttaaccttac aacgccaaag aagtctggcg tgttgagaga ctattcagct tgtgacggat    60
aagacctgtg gccgtgaggc ggcaggtgac agaatttgcc tggcggctgt agcgcggtgg   120
tccca                                                              125

<210> SEQ ID NO 20
<211> LENGTH: 23
<212> TYPE: DNA
<213> ORGANISM: Synthliboramphus antiquus

<400> SEQUENCE: 20
gaggcggcag gtgacagaat ttg                                           23

<210> SEQ ID NO 21
<211> LENGTH: 20
<212> TYPE: DNA
<213> ORGANISM: Synthliboramphus antiquus

<400> SEQUENCE: 21
acggataaga cctgtggccg                                               20

<210> SEQ ID NO 22
<211> LENGTH: 22
<212> TYPE: DNA
<213> ORGANISM: Synthliboramphus antiquus

<400> SEQUENCE: 22
cgccattgtg cgaggatggt gc                                            22

<210> SEQ ID NO 23
<211> LENGTH: 20
<212> TYPE: DNA
<213> ORGANISM: Synthliboramphus antiquus

<400> SEQUENCE: 23
caagtcgaac ggtaacaggg                                               20

<210> SEQ ID NO 24
<211> LENGTH: 18
<212> TYPE: DNA
<213> ORGANISM: Synthliboramphus antiquus

<400> SEQUENCE: 24
gtcccccact ttggtccg                                                 18

<210> SEQ ID NO 25
<211> LENGTH: 28
<212> TYPE: DNA
<213> ORGANISM: Synthliboramphus antiquus

<400> SEQUENCE: 25
atctcaaaam tgactgtaaa gtcacgtt                                      28

<210> SEQ ID NO 26
<211> LENGTH: 23
<212> TYPE: DNA
<213> ORGANISM: Synthliboramphus antiquus
```

```
<400> SEQUENCE: 26
ccgaaraagt mttcgkgctg cga                                             23

<210> SEQ ID NO 27
<211> LENGTH: 82
<212> TYPE: DNA
<213> ORGANISM: Synthliboramphus antiquus

<400> SEQUENCE: 27
ttaaccttac aacgccaaag aagtctggcg tgttgagaga caattcagct tgtgacggat     60
aaacgttcat ggcggaagcg gt                                              82

<210> SEQ ID NO 28
<211> LENGTH: 84
<212> TYPE: DNA
<213> ORGANISM: Synthliboramphus antiquus

<400> SEQUENCE: 28
ttaaccttac aacgccgaag gtgttttggc gtgatttgag agaaattcag cttgtgacgg     60
atacagcctg tggccggaag tggc                                            84

<210> SEQ ID NO 29
<211> LENGTH: 84
<212> TYPE: DNA
<213> ORGANISM: Synthliboramphus antiquus

<400> SEQUENCE: 29
ttaaccttac aacgccgaag atgttttggc gtgatttgag agaaattcag cttgtgacgg     60
ataaccactc atggcgcaag cggt                                            84

<210> SEQ ID NO 30
<211> LENGTH: 84
<212> TYPE: DNA
<213> ORGANISM: Synthliboramphus antiquus

<400> SEQUENCE: 30
ttaaccttac aacgccgaag gtgttttggt gttgtatttg agagattttc agcttgagac     60
ggattaaacc tgtggccgtg cggc                                            84

<210> SEQ ID NO 31
<211> LENGTH: 43
<212> TYPE: DNA
<213> ORGANISM: Synthliboramphus antiquus

<400> SEQUENCE: 31
gaacggacag aatttgcctg gcggctgtag cgcggtggtc cca                       43

<210> SEQ ID NO 32
<211> LENGTH: 46
<212> TYPE: DNA
<213> ORGANISM: Synthliboramphus antiquus

<400> SEQUENCE: 32
ggcaggtgaa cagaatttgc ctggcggccg tagcgcggtg gtccca                    46

<210> SEQ ID NO 33
<211> LENGTH: 43
<212> TYPE: DNA
<213> ORGANISM: Synthliboramphus antiquus

<400> SEQUENCE: 33
```

-continued

```
gagtgaacaa aatctgcctg gcggccgtag cgcggtggtc cca        43

<210> SEQ ID NO 34
<211> LENGTH: 46
<212> TYPE: DNA
<213> ORGANISM: Synthliboramphus antiquus

<400> SEQUENCE: 34
ggcaggtgaa cagaatttgc ctggcggctg tagcgcggtg gtccca     46

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
caagtcgaac ggtaacaggg                                  20

<210> SEQ ID NO 36
<211> LENGTH: 18
<212> TYPE: DNA
<213> ORGANISM: Artificial Sequence
<220> FEATURE:
<223> OTHER INFORMATION: Synthetic

<400> SEQUENCE: 36
gtcccccact ttggtccg                                    18

<210> SEQ ID NO 37
<211> LENGTH: 28
<212> TYPE: DNA
<213> ORGANISM: Artificial Sequence
<220> FEATURE:
<223> OTHER INFORMATION: Synthetic

<400> SEQUENCE: 37
atctcaaaam tgactgtaaa gtcacgtt                         28

<210> SEQ ID NO 38
<211> LENGTH: 23
<212> TYPE: DNA
<213> ORGANISM: Artificial Sequence
<220> FEATURE:
<223> OTHER INFORMATION: Synthetic

<400> SEQUENCE: 38
ccgaaraagt mttcgkgctg cga                              23
```

NUCLEIC ACIDS AND METHODS FOR THE DETECTION OF *ENTEROBACTER SAKAZAKII* (*CRONOBACTER* SPP.)

CROSS-REFERENCE TO RELATED APPLICATIONS

This patent application is a continuation of U.S. application Ser. No. 13/389,366, filed Apr. 16, 2012, which is the U.S. national phase of PCT/EP2010/004794, filed Aug. 4, 2010, which claims priority to European Application No. 09010239.3, filed Aug. 7, 2009. The disclosures of each of these applications are incorporated herein by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 7,238 bytes ASCII (Text) file named "719176SequenceListing-3rd_ST25.txt" created Jun. 16, 2022.

BACKGROUND OF THE INVENTION

*Enterobacter sakazakii* is a pathogen of the Enterobacteriaceae family which is able to cause different diseases like necrotising enteritis, meningitis or septicemia and infects particularly prematured babies and infants with low immunity.

In comparison to other infections the official number of published *E. sakazakii* outbreaks is rather low, but the progressive course of *E. sakazakii*-induced diseases is often dramatic which is pointed out by a death rate of 40-80%.

Among several environmental origins of infection, milk-powder based baby food could be identified as a major source several times.

The shown coherence (FAO/WHO 2004, 2006) between the appearance of *E. sakazakii* in infant formulae and the coincidental occurrence of diseases has resulted in the current European regulation Nr. 2073/2005 which is defining microbiological criteria for foodstuffs. Therefore, *E. sakazakii* should not be detected in 300 g (n=30, c=0, m=negativ/10 g) dried infant formulae and dietary foods with special medical relevance which is to be designed for infants under the age of 6 months.

The primary edition of this regulation has resulted in an inspection requirement for *E. sakazakii* if the microbiological criterion for Enterobacteriaceae (negative results for 10 samples; starting material: 10 g) was not complied. However, an expertise of the european board for food safety has shown no general occurrence of Enterobacteriaceae and *E. sakazakii* at the same time. As a consequence, detections for Enterobacteriaceae and *E. sakazakii* must be done separately according European regulation Nr. 1441/2007. An exception is made if the individual company is able to document an explicit relationship between the appearance of Enterobacteriaceae and *E. sakazakii*.

As *E. sakazakii* strains are characterized by a diverse pheno- and genotypical heterogeneity, a taxonomic reclassification of *E. sakazakii* was accomplished. From this follows that the new introduced genus of *Cronobacter* contains the species *C. sakazakii*, *C. malonaticus*, *C. muytjensii*, *C. turicensis* and *C. dublinensis* as well as the three subspecies *C. dublinensis* subsp. *dublinensis*, *C. dublinensis* subsp. *lausannensis* and *C. dublinensis* subsp. *lactaridi*. In addition, two more strains are currently named as C. genomospecies 1 although they could not be allocated to these species.

As clinical isolates could be found in all different species of *Cronobacter*, a potential danger of the whole genera could be assumed. Therefore, the regulations developed for *E. sakazakii* could be transferred on *Cronobacter* spp. (Iversen et al., 2007, BMC Evol Biol. 7: 64).

TECHNOLOGY UP-TO-DATE

In the regulation 2073/2005 the international prestandard ISO/TS 22964 is mentioned as cultural method for the standard detection of *E. sakazakii* (*Cronobacter* spp.). This procedure includes an isolation based on chromogenic selection media after pre-enrichment in buffered peptone water and a selective enrichment in modified LST-Bouillon. Candidates will be checked if a characteristic yellow colouration can be recognized after inoculation on TSA-Agar. The yellow colonies must be confirmed by biochemical tests. This method is time- and laborintensive and can produce false-negative results. For example, some *Cronobacter* strains are not forming yellow colonies on TSA-Agar. (Besse et al., 2006, J. AOAC Int. 89: 1309-1316; Iversen et al., 2004, J. Clin. Microbiol. 42: 5368-5370).

Iversen et al. (2007, J. Clin. Microbiol. 45: 3814-3816) has shown that none of three tested chromogenic *Cronobacter* agars enable the detection of all *Cronobacter* strains. In the same study only 70 and 90% of the *Cronobacter* strains could be identified as *E. sakazakii* by biochemical tests API20E and ID32E. Another disadvantage of this cultural detection method is reasoned in a false-positive identification of some Enterobacteriaceae by using chromogenic or TSA-Agar and the API20E test kit (Iversen et al., 2007, J. Clin. Microbiol. 45: 3814-3816).

In comparison to these often variable phenotype-dependent cultural methods, molecular biological detection methods which are based on the hybridization of DNA-probes turned out to be more specific generally. These molecular biological detection methods are very sensitive and allow a fast detection of the microorganisms.

Especially methods which are combining an enrichment of nucleic acids and the detection by DNA-probes have gained more importance whereas the polymerase-chain-reaction (PCR) could be stated as very well-known example.

Several PCR-systems for the detection of *E. sakazakii*/ *Cronobacter* spp. are already described. Here, the gene region rpsUIdnaG (Seo & Brackett, 2005, J Food Prot. 68: 59-63) and the genes gluA (Lehner et at, 2006, BMC Microbiol. 6: 15), ompA (Nair & Venkitanarayanan, 2006, Appl. Environ. Microbiol. 72: 2539-46) and zpx (Kothary et al., 2007, Appl. Environ. Microbiol. 73: 4142-51) served as DNA target sequences as well as parts of the ribosomal operon 16S rDNA (Lehner et al., 2004, BMC Microbiol. 4: 43; Malorny & Wagner, 2005, J. Food Prot. 68: 1623-1627; Hassan et al., 2007, Int. J. Food Microbiol. 116: 214-20) and the DNA-sequence between the tRNA-glu and 23S rDNA gene (Derzelle & Dilasser, 2006, BMC Microbiol. 6: 100).

In most cases only a limited number of *Cronobacter* strains were tested by these PCR-systems which are not covering the genetic diversity of the whole genus. In addition, the detection of members of the newly-described *Enterobacter*-species *E. helveticus* and *E. pulveris* were not tested although the organisms are closely related to the genus *Cronobacter*.

Cawthorn et al. (2008, Int. J. Food Microbiol. 127: 129-38) determined a specificity of max. 92% as they have compared 6 different PCR-systems in total which were described in the literature.

Iversen et al. (2007, J. Clin. Microbiol. 45: 3814-3816) found out a specificity of each 100% for 2 PCR-systems which were based on the rpsU/dnaG gen region. But in opposite to the ribosomal operons both gene regions only exist as single copy versions in the *Cronobacter* genom. (McClelland et al., 2008, GenBank accession number NC009778). As in total seven copies of the ribosomal operon could be found in the genome, a PCR-system which is built up on this genome region guarantees a significant higher sensitivity limit. Generally, a maximum of sensitivity is a very important feature for the detection of *Cronobacter* cells in contaminated infant formulae as the concentration of cells is quite low normally. (FAO/WHO 2006)

The regulation (EU) Nr. 1441/2007 rules that milk-powder based infant formulae must be analyzed for Enterobacteriaceae and *E. sakazakii* in parallel if a clear relationship between the occurance of Enterobacteriaceae and *E. sakazakii* could not be found out. Cultural methods allow just a separate detection of the two parameters. In case of reference standards for *E. sakazakii* and Enterobacteriaceae only an enrichment in buffered peptone water is identically. The selective enrichment steps, isolation and identification have to be done separately. At the moment no biochemical or molecular biological method for the simultaneous detection of both parameters is described.

In comparison to cultural techniques, a drawback of molecular biological DNA-based methods like PCR is the non-selective detection of DNA from living and dead cells. By use of PCR a positive analysis result is often possible if only dead cells are in the sample, due to the high stability of DNA.

There have been a lot of methods developed in the past to circumvent this disadvantage of a PCR-based detection of microorganisms. Due to the less stability, one approach is the use of RNA instead of DNA as the target molecule. Detection will be accomplished by reverse transcription following PCR of the generated cDNA. But ribosomal RNA is not suitable as a viability marker, because of its high stability. Messenger RNA is in general much more unstable, but the detection of mRNA is sophisticated because of the omnipresent RNase and so only limited suitable for routine testing.

Recently were alternative methods published to selective amplify DNA of viable microorganisms. This selectivity will be achieved by compounds that can only penetrate cells with compromised cell walls and cell membranes. These compounds are phenanthridinium derivates with a light-sensitive azide group that can be covalently linked to DNA by photoactivation whereby amplification will be inhibited with high efficiency (Rudi et al., 2005, Appl. Environ. Microbiol. 71: 1018-1024; Nocker et al., 2006, J Microbiol Methods 67: 310-320).

DETAILED DESCRIPTION OF THE INVENTION

The object of this invention is to provide a detection method which is 100% specific for the genus *Cronobacter* (*E. sakazakii*) and at the same time very sensitive by using a target molecule which is multiple existent in *Cronobacter* cells. The complete coverage of the genus *Cronobacter* is very important, because all species are considered to be hazardous pathogens. On the other hand a false-positive detection of other bacteria like the closely related, non-pathogenic species *E. helveticus* or *E. pulveris*, which often mimic a presence of *Cronobacter*, has to be avoided. Such false-positive results are able to cause high economic losses. In most cases, the number of *Cronobacter* cells in contaminated samples is extremely low. Therefore a detection method has to be as sensitive as possible.

The inventors have surprisingly found out, that oligonucleotides or combinations thereof targeting the multi copy existing genomic region from the 3'-end of the 23S-till the 5'-end of the 5S-rDNA gene including the internal transcribed spacer region (ITS 2) enable such a specific and sensitive detection of *Cronobacter* spp.

They also discovered two oligonucleotides targeting this region that allow a specific detection of a subgroup of *C. turicensis*. FIG. 1 shows the DNA region as well as the hybridization positions of the oligonucleotides of this invention.

SEQ ID NO: 1:
TTA ACC TTA CAA CGC CAA AGA AGT CTG GCG TGT TGA GAG ACA ATT CAG CTT GTG ACG GAT ARA CGT TCA TGG CGG AAG CGG TGR ACG RAC AGA ATT TGC CTG GCG GCT GTA GCG CGG TGG TCC CA

SEQ ID NO: 1 comprises the 23S-ITS2-5S region of *Cronobacter* spp. (except for one subgroup of *Cronobacter turicensis*).

SEQ ID NO: 2: ACC TTA CAA CGC CAA AGA AGT C
SEQ ID NO: 3: TGT AGC GCG GTG GTC C
SEQ ID NO: 4: AAG CGG TGA ACG GAC AGA ATT TGC CTG GC
SEQ ID NO: 5: AAG CGG TGG ACG GAC AGA ATT TGC CTG GC
SEQ ID NO: 6: AAG CGG TGA ACG AAC AGA ATT TGC CTG GC
SEQ ID NO: 7: AAG CGG TGG ACG AAC AGA ATT TGC CTG GC
SEQ ID NO: 8: TTC AGC TTG TGA CGG ATA AAC GTT CAT GGC G
SEQ ID NO: 9: TTC AGC TTG TGA CGG ATA GAC GTT CAT GGC G
SEQ ID NO: 10: GAA GTC TGG CGT GTT GAG AGA CPA T
SEQ ID NO: 11: AAA CGT TCA TGG CGG AAG CGG TGA ACG AAC A
SEQ ID NO: 12: AGA CGT TCA TGG CGG AAG CGG TGA ACG AAC A
SEQ ID NO: 13: AGA CGT TCA TGG CGG AAG CGG TGG ACG AAC A
SEQ ID NO: 14: AGA CGT TCA TGG CGG AAG CGG TGG ACG GAC A
SEQ ID NO: 15: AAA CGT TCA TGG CGG AAG CGG TGG ACG AAC A
SEQ ID NO: 16: AAA CGT TCA TGG CGG AAG CGG TGA ACG GAC A
SEQ ID NO: 17: AAA CGT TCA TGG CGG AAG CGG TGG ACG GAO A
SEQ ID NO: 18: AGA CGT TCA TGG CGG AAG CGG TGA ACG GAC A
SEQ ID NO: 2-18 are derived from SEQ ID NO: 1.
SEQ ID NO: 19:
TTA ACC TTA CM CGC CPA AGA AGT CTG GCG TGT TGA GAG ACT ATT CAG CTT GTG ACG GAT MG ACC TGT GGC CGT GAG GCG GCA GGT GAC AGA ATT TGC CTG GCG GCT GTA GCG CGG TGG TCC CA SEQ ID NO: 19 comprises the 23S-ITS2-5S region of *E. sakazakii* LMG 2790 (*C. turicensis*). The strain LMG 2790 was reclassified to *C. turicensis* by the inventors after sequencing of a part of the 16S rDNA gene and sequence comparison to GENBANK database.
SEQ ID NO: 20: GAG GCG GCA GGT GAC AGA ATT TG
SEQ ID NO: 21: ACG GAT AAG ACC TGT GGC CG
SEQ ID NO: 20-21 are derived from SEQ ID NO: 19.
SEQ ID NO: 22: CGC CAT TGT GCG AGG ATG GTG C
SEQ ID NO 22 is an oligonucleotide with an artificial sequence complementary to an amplification control nucleic acid.

Definitions

Fragments of Oligonucleotides

Fragments of oligonucleotides arise due to deletion of one or more nucleotides on the 5' and/or 3' end of an oligonucleotide.

Identical DNA Sequences/Percentage of Identity

For the determination of the identity (in the sense of complete matching, corresponding to 100% identity) of DNA or RNA sequences, partial sequences of a larger polynucleotide are considered. These partial sequences comprise ten nucleotides and are then identical when all 10 modules are identical for two comparative sequences. The nucleotides thymidine and uridine are identical. As partial sequences, all possible fragments of a larger polynucleotide can be considered.

As an example two polynucleotides are considered which comprise 20 nucleotides and which differ in the 5th module. In a sequence comparison six 10-way nucleotides are found which are identical and five which are not identical, because they differ in one module.

In addition, the identity can be gradually determined, whereby the unit is stated in percent. For the determination of the degree of identity partial sequences are also considered, which comprise as a minimum the length of the actually used sequence, e.g. as primer, or 20 nucleotides.

As an example, polynucleotide A with a length of 100 nucleotides and B with a length of 200 nucleotides are compared. A primer with a length of 14 nucleotides is derived from polynucleotide B. For the determination of the degree of identity, polynucleotide A is compared with the primer over its complete length. If the sequence of the primer occurs in polynucleotide A, whereby it however deviates in one module, then there is a fragment with a degree of identity of 13:14.fwdarw.92.3%.

In the second example the polynucleotides A and B previously mentioned are compared in their entirety. In this case all the possible comparative windows of a length of 20 nucleotides are applied and the degree of identity determined for them. If then nucleotides nos. 50-69 of polynucleotide A and B are identical with the exception of nucleotide no. 55, then a degree of identity of 19:20.fwdarw.95% arises for these fragments.

Multiplex PCR

A multiplex PCR is a Polymerase Chain Reaction or DNA or RNA amplification reaction in which more than two primers are used which are not regarded as a forwards-backwards primer pair. With the presence of all nucleotide target molecules to be detected, this leads to the creation of at least two different amplicons. These amplicons should at least differ in the region in which the primers link, but they can also be allocated to completely different genes.

Nucleotides

Nucleotides are the modules of the DNA or RNA. The following abbreviations are used:
G=Guanosine, A=Adenosine, T=Thymidine, C=Cytidine,
R=G or A, Y=C or T,
K=G or T, W=A or T, S=C or G, M=A or C, B=C, G or T,
D=A, G or T, H=A, C or T,
V=A, C or G, N=A, C, G or T, I=Inosine.

Real-Time Detection

In relation to this invention, real-time detection is defined as the simultaneous running of two processes: the detection of the DNA or RNA and a process which leads to the provision of a detectable amount of DNA or RNA. With this process the release of genomic DNA/RNA from cells may, for example, be involved or the enrichment of DNA/RNA from a complex mixture or the amplification of polynucleotides, e.g. through a PCR. Detection is the perception of a signal which correlates to the presence and possibly the amount of the DNA/RNA. In the case of the PCR this type of signal may increase with the increasing amplification of the target DNA. Real-time detection can be carried out also in a miniaturised form, e.g. on a chip. The signal can, for example, be produced through the fluorescent molecules of a probe, through radioactive molecules or through enzyme-coupled colour or fluorescence intensity.

The term real-time detection is synonymous to on-line detection.

Nucleic Acid

A "nucleic acid" is a DNA, RNA, PNA, or LNA which is obtained either through isolation from genomic DNA or from cDNA according to known standard methods and purified or generated artificially using known methods such as oligonucleotide synthesis or isolated as ribosomal RNA or mRNA from the organism or synthesised as PNA or LNA.

A "PNA" is a peptide nucleic acid in which instead of the phosphoric acid backbone of the DNA, 2-aminoethylglycin compounds occur.

A "LNA" is a locked nucleic acid in which the pentose moiety of DNA or RNA is modified to contain a 2'-O, 4'-C methylene linkage (1,2:5,6-di-O-isopropylene-alpha-D-allo-furanose) to "lock" the nucleic acid in a certain conformational state.

According to the invention, in the nucleic acids, up to 20% of the nucleotides in 10 consecutive nucleotides, preferably however 1 nucleotide from a block of 10 consecutive nucleotides, may be replaced by nucleotides (e.g. inosin, etc.) which do not naturally occur in bacteria.

The nucleic acids may further contain modifications which allow the production of a signal that can be detected directly or indirectly. The expert is aware of the following modifications here:
(i) radioactive modifications, i.e. radioactive phosphorylation or radioactive marking with sulphur, hydrogen, carbon, nitrogen;
ii) colored groups (e.g. digoxygenin, etc.);
(iii) fluorescent groups (e.g. fluorescein, etc.);
(iv) chemoluminescent groups;
(v) groups for the immobilisation at a solid phase (e.g. biotin, streptag, antibodies, antigens, etc.); and/or
(vi) groups which allow an indirect or direct reaction with the help of antibodies, antigens, enzymes and/or substances with an affinity to enzymes or enzyme complexes;
or combinations of modifications according to two or more of the modifications listed under (i) to (vi). The term "modification" as used in this invention is understood to mean directly or indirectly detectable groups or groups for immobilisation at a solid phase which are attached to the nucleic acid. Metal atoms, radioactive, colored or fluorescent groups are directly detectable groups. Immunologically or enzymatically detectable groups are indirectly detectable groups, such as antigens and antibodies, haptenes or enzymes or parts of enzymes with an enzymatic effect.

These indirect groups are detected in subsequent reactions. Preference is given to haptenes which are linked to an oligonucleotide and which are detected in a subsequent antibody reaction.

Primer

Primers are oligonucleotides which act as starter molecules during a PCR. Here, they hybridise on a target molecule, which may be, for example, DNA or RNA, and are lengthened by a polymerase. They can also however act as probes.

Probe

Probes are oligonucleotides or polynucleotides which hybridise on the target DNA or RNA molecules. They are used for the direct or indirect detection of these target DNA or RNA molecules. For this purpose, they can be coupled to fluorescent molecules or to molecules containing colouring agents. In addition they can be indirectly detected with an ELISA. In a special version they only produce a signal through FRET (Fluorescence Resonance Energy Transfer) when two probes hybridise adjacently in a defined manner. In this case a colouring agent on a probe is excited by a light beam and transfers its excitation energy to the colouring agent of the adjacent probe. This then emits light of a defined wavelength. In another special version signal generation relies on the 5'-3' nuclease activity of Taq polymerase to cleave a dual-labelled probe during hybridization to the complementary target sequence. These dual-labelled probes consist of a fluorophore covalently attached to the 5'-end of the oligonucleotide probe and a quencher at the 3'-end. As long as the fluorophore and the quencher are in proximity, quenching inhibits any fluorescence signals. As the Taq polymerase extends the primer and synthesizes the nascent strand, the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore.

Derivatives of the Oligonucleotides According to the Invention

Variations, Variants or derivatives of the oligonucleotides according to the invention are taken to mean sequences which differ in at least one nucleotide from the specific sequences according to SEQ ID numbers 1-22, for example, by at least one base interchange, an insertion, deletion or addition. These also include oligonucleotides which are at least 80% identical to one of the specific sequences according to SEQ ID numbers 1-22 and oligonucleotides with a comparable specificity of hybridisation. The latter signifies that the variation produces the same hybridisation pattern with a specified sample containing nucleic acid, such as the oligonucleotide with one of the specific sequences with one of the SEQ ID numbers 1-22.

Throughout the application, variants of any nucleic acid molecule of any of SEQ ID NO 1-22 are contemplated as alternatives to the respective oligonucleotide of SEQ ID NO 1-22. A variant of a nucleic acid molecule of any of SEQ ID NO 1-22 is a) a nucleic acid molecule which hybridizes under specific conditions with the respective nucleic acid molecule of any of SEQ ID NO 1-22;
b) a nucleic acid molecule which is at least 70%, 80% or 90% identical with the nucleic acid molecule of a); or
c) the complement of the nucleic acid molecule of SEQ ID NO 1-108 or of one of the variants a) to b).

Particular variants are also defined under "embodiments of the invention".

Biochip

Biochip is taken to mean carriers for the high throughput of analyses as marketed, for example, by AFFYMETRIX. The chips enable the testing of numerous different nucleic acids on one carrier.

Hybridisation

The term "hybridisation" is understood as the double strand formation of two identical or similar nucleic acid fragments (DNA, RNA, PNA, LNA). Specific hybridisation is the term used if the hybridisation is carried out under strict conditions and gives a stable hybrid nucleic acid. In the terms of this invention, the feature "sequence which specifically hybridises with a sequence according to (i)" refers to a sequence which hybridises under strict conditions with the sequence according to (i).

The stringency of the hybridization conditions depends on various factors such as the base composition of the hybrid, the level and geometry of mispairing between the two nucleic acids, as well as reaction parameters like ionic strength and the reaction temperature. Appropriate conditions can be determined based on thermodynamic calculations (Santa Lucia et. al. 1996), which have been incorporated into a variety of computer programs known to those skilled in the art. Examples of stringent conditions are set forth in the example section below.

Melting Curves and Melting Temperature

In relation to this invention, a melting curve analysis of a sample is defined as the following sequence of processes: the heating of the sample to a temperature high enough to denature the DNA in the sample; the cooling of the sample to a temperature below the annealing temperature of the target DNA; a slow heating of the sample with the simultaneous (real-time, online) detection of the dissociation (i.e., melting) of the DNA. Detection is the perception of a signal which correlates to the proportion of dissociated and not yet dissociated DNA. In the case of a melting curve after a PCR with hybridization probes or with a double strand binding dye, this type of signal may decrease with the increasing temperature. An inflexion point of the signal course is defined as melting temperature. The melting temperature of a sample is the point at which half the probes or the double strand binding dye have melted off the target DNA. For a better visualization, the first negative derivative of the signal course can be plotted against the temperature; the melting temperatures then appear as peaks of the curve. A melting curve can also be carried out in a miniaturised form, e.g. on a chip.

With a preferred embodiment the nucleic acid to be examined is passed to a PCR. This has the result that Cronobacter-specific amplicons are produced if nucleic acids of Cronobacter bacteria are present in the sample. Here in the simplest case, the PCR can be arranged as a simple linear PCR with only one oligonucleotide as primer, but preferably the PCR takes place however with so-called forwards and backwards primers for each genome section of the bacterial nucleic acid to be amplified.

With a further preferred embodiment various oligonucleotides and therefore various PCR runs are carried out in the form of a multiplex PCR. Here, different amplicons are created in the PCR in a single initiated reaction with the aid of the various oligonucleotides. Especially meaningful is the combination of oligonucleotides of this invention specific for the genus Cronobacter with oligonucleotides for the detection of the whole family Enterobacteriaceae because according to directive (EU) nr. 1441/2007 milk-based infant formula has to be analysed for Enterobacteriaceae and *E. sakazakii* in parallel unless a direct correlation could be found.

With a further preferred embodiment use is made of the so-called chip technology (biochips) in the detection method. Here, on one hand a large number of different analysis samples can be analysed on one chip in that the individual spots on the chip contain analysis material from different sources. On the other hand, the chip can carry a set of oligonucleotides, whereby each spot contains a specific oligonucleotide and this oligonucleotide pattern is brought into contact with analysis samples. In the case that the analysis material contains *Cronobacter* nucleic acid, it hybridises with the probes specific to the *Cronobacter* present on the chip and produces a corresponding signal pattern.

With a further preferred embodiment the detection method can include further steps, such as for example an amplification of the nucleic acid to be detected, whereby this preferably occurs using PCR and/or a southern hybridisation with *Cronobacter*-specific probes, whereby this hybridisation occurs without prior amplification or after amplification of the nucleic acid to be detected is concluded. Furthermore, the nucleic acid to be detected can be detected using the ligase chain reaction. Finally, the nucleic acid to be detected can be enriched by isothermal nucleic acid amplification.

With a further preferred embodiment, the amplification of the target nucleic acid can also take place using real-time detection.

With a further preferred embodiment the amplification of the nucleic acid to be detected and/or the detection of the contained amplicons occur on a biochip, whereby it is particularly preferable to carry out the amplification and detection on one chip.

According to the invention, as a means for carrying out the method described above, oligonucleotides are selected from a nucleic acid, comprising at least one sequence with one of the SEQ ID numbers 1-22 or variations thereof. The stated oligonucleotides can on one hand be used as primers within the scope of a PCR and on the other hand also as probes, for example within the scope of a southern blot hybridisation. Depending on the requirements of the desired detection, the specialist can form the suitable combination of oligonucleotides as primers or probes. Preferably, the stated oligonucleotides or combinations of them are used in the form of a kit for the detection of *Cronobacter* spp., whereby the kit also includes other reagents for the detection of bacteria or for conducting the detection reactions. In this respect, the reagents and enzymes required for the PCR and, where applicable, suitable carrier materials are also included, for example, such as it is desired with the chip technology.

The oligonucleotides or oligonucleotide combinations according to the invention are therefore a suitable means for the specific and reliable detection of *Cronobacter* spp. in any analysis samples.

With the invention of the polymerase chain reaction it is possible to amplify individual DNA polynucleotides and then to detect them with extremely high sensitivity. This technology opens up substantial new opportunities, but also exhibits new problems. For example, with the DNA amplification incorrect fragments can be easily amplified, leading to incorrect positive results in the analysis. In addition, it is very difficult to select the diagnostic DNA sequences characteristic to *Cronobacter* from the multitude of possibilities.

This invention consists of a method and oligonucleotides which enable a qualitative and quantitative detection of *Cronobacter* spp. The detection method consists all together of four steps: propagation of the bacteria, purification of the DNA/RNA, amplification of the polynucleotides and detection of them. In a special method the two last steps can also take place simultaneously.

The propagation of the bacteria occurs in that the matrix to be investigated, e.g. an infant formula sample is incubated with a currently available bacterial medium. Bacterial media are commercially available and can, for example, contain a proteolytically digested basic substance, such as peptone broth, and a buffer such as dipotassium hydrogen phosphate.

In the second step the polynucleotides are purified. To do this, the bacteria are normally first separated from the medium by centrifuging and/or filtration. A further washing stage may follow. Then the bacteria are broken down. This takes place by heating, by an alkaline or acidic environment or by reagents which destabilise the bacteria cell wall, such as deionising chemicals or lysozyme. The genomic DNA or the RNA can now be directly used in a PCR reaction or it is purified further. For this purification materials are suitable on the surface of which the polynucleotides bond, e.g. positively charged surfaces or silicate surfaces. This material can be mounted in columns and is commercially available.

To avoid an amplification of DNA from dead cells the cells could be treated with phenanthridinium derivates with a light-sensitive azide group like ethidium monoazide bromide (EMA) or propidium monoazide bromide (PMA) before the DNA isolation procedure starts. This treatment consists of two steps. In the first step cells and phenanthridinium derivates are incubated together in the dark to allow these compounds to penetrate cells with compromised cell membranes. Afterwards this mixture will be placed under a high power light bulb and the light-sensitive azide group react with the DNA. By this covalent bond an amplification of the DNA will be inhibited.

The PCR reaction and the detection of the amplicons have great importance in the detection of bacteria. As already explained, it is very difficult to find differences in DNA sequences between the genus *Cronobacter* and other bacteria, in particular closely related species like *E. helveticus* and *E. pulveris*.

To avoid false negative results, in a preferred embodiment of the invention, an amplification control nucleic acid is added during amplification. Accordingly, not only the microbial nucleic acid or a part thereof is amplified, but also the amplification control nucleic acid, which means that at least one amplification fragment in each case is created. The amplification control nucleic acid, e.g. a DNA fragment, is here an "internal standard molecule" which serves as an indicator for the effectiveness of the reaction (Ballagi-Pordany, Belak, 1996, Mol. Cell. Probes 10, 159-164). It is added in a defined quantity to the amplification reaction and amplified in parallel. The amplification control nucleic acid is preferably single or double strand and may be of unlimited length. Amplification control nucleic acids with a length of up to a thousand nucleotides have proved successful. In a preferred embodiment of this invention, the amplification control nucleic acid contains a sequence that is identical or complementary to the sequence of SEQ ID NO 22 or a part of it.

For good laboratory praxis in a diagnostic procedure it is recommended to monitor the whole analytical process by using external positive controls. In the case of the detection of *Cronobacter* spp. according to this invention the analysis of an additional positive control sample containing *Cronobacter* cells enables to check the complete process comprising microbial enrichment, DNA isolation and PCR. A drawback of the application of such a positive control is the possibility to get false-positive results due to cross-contamination by the positive control. False-positive results could be avoided by using of a positive control that can be differentiated from a true contamination by *Cronobacter* bacteria. A further embodiment of this invention is the discrimination of a rare subgroup from most common *Cronobacter* strains. This discrimination is possible via melting curve analysis using SEQ ID NO 4-7 and SEQ ID NO 8-9 or via direct detection of a subgroup of *C. turicensis* using SEQ ID NO 19-21.

Embodiments of the Present Invention are:
1. Nucleic acid molecule suitable as primer or probe in the detection of the genus *Cronobacter*, wherein
   i) the nucleic acid molecule
      a) is a sequence comprising or consisting of a partial sequence of SEQ ID NO: 1, which partial sequence is highly conserved or conserved in all species of the genus *Cronobacter*; and
      b) is between 10-50, preferably 15-40 and more preferably 20-35 nucleic acids long;
   ii) the nucleic acid molecule
      a) is a sequence which hybridizes under specific or stringent conditions with the nucleic acid molecule of i); and
      b) is between 10 and 50, preferably 15-40 and more preferably 20-35 nucleic acids long; or
   iii) the nucleic acid molecule
      a) is at least 70, 75, 80, 85, 90 or 95% identical with the nucleic acid molecule, wherein identity may be determined over the stretch of at least 15, 20 or 25, preferably 15-50 nuclei acids, more preferably 15-40 and most preferably 20-35 nucleic acids; and
      b) is between 10 and 50, preferably 15-40 and more preferably 20-35 nucleic acids long; or
   iv) the nucleic acid molecule is the complement of the nucleic acid molecule of any of i) to iii).

"Highly conserved" in embodiment 1 means suitable to hybridize under stringent conditions (59° C.-66° C.) with all members of the genus *Cronobacter*; at least with *C. sakazakii, C. malonaticus, C. muytjensii, C. dublinensis, C.* genomospecies 1 and preferably all or at least parts of the species *C. turicensis*; preferably not more than 4, 3, 2 or 1 mismatches in a stretch of 20 nucleotides occur with SEQ ID NO: 1; the highly conserved sequence may be a degenerate sequence.

"Conserved" in embodiment 1 means suitable to hybridize only under non-stringent conditions (50° C.-55° C.) with a subgroup of the species *C. turicensis*. "Conserved" sequences hybridize under stringent conditions (59° C.-66° C.) with the members of the genus *Cronobacter C. sakazakii, C. matonaticus, C. muytjensii, C. dublinensis, C.* genomospecies 1.

2. The nucleic acid molecule of embodiment 1, which is
   a) selected from SEQ ID NOs: 2, 3, which are primers, 4-7, which are degenerate probes; 8-9, which are degenerate probes, 10, which is a probe, or 11-18, which are degenerate probes; or
   b) a sequence which hybridizes under specific conditions with the nucleic acid molecule of a);
   c) at least 70, 75, 80, 85, 90 or 95% identical with the nucleic acid molecule of a), wherein identity may be determined over the stretch of at least 15, 20 or 25 preferably 15-50 nuclei acids, more preferably 15-40 and most preferably 20-35 nucleic acids; or
   d) the complement of the nucleic acid molecule of any of a) to c).

3. Nucleic acid molecule suitable as probe in the detection of a subgroup of *Cronobacter*, namely the species *Cronobacter turicensis*, wherein these probes may but do not have to detect all strains of *Cronobacter turicensis* and wherein
   i) the nucleic acid molecule
      a) is a sequence comprising or consisting of a partial sequence of SEQ ID NO: 19, which partial sequence is highly conserved a subgroup of the species *C. turicensis*; and
      b) is between 10 and 50, preferably 15-40, more preferably 20-35 nucleic acids long;
   ii) the nucleic acid molecule
      a) is a sequence which hybridizes under specific conditions with the nucleic acid molecule of i); and
      b) is between 10 and 50 preferably 15-40, more preferably 20-35 nucleic acids long; or
   iii) the nucleic acid molecule
      a) is at least 70, 75, 80, 85, 90 or 95% identical with the nucleic acid molecule, wherein identity may be determined over the stretch of at least 15, 20 or 25 preferably 15-50 nuclei acids, more preferably 15-40 and most preferably 20-35 nucleic acids; and
      b) is between 10 and 50, preferably 15-40, more preferably 20-35 nucleic acids long; or
   iv) the nucleic acid molecule is the complement of the nucleic acid molecule of any of i) to iii).

"Highly conserved" in embodiment 3 means suitable to hybridize under stringent conditions (59° C.-64° C.) with a subgroup of the species *C. turicensis* (for the subgroup of the species *C. turicensis* see e.g. example 3).

4. The nucleic acid molecule of embodiment 3, which is
   a) selected from SEQ ID NOs: 20-21, which are probes; or
   b) a sequence which hybridizes under specific conditions with the nucleic acid molecule of a);
   c) at least 70, 75, 80, 85, 90, or 95% identical with the nucleic acid molecule of a), wherein identity may be determined over the stretch of at least 15, 20 or 25 preferably 15-50 nuclei acids, more preferably 15-40 and most preferably 20-35 nucleic acids; or
   d) the complement of the nucleic acid molecule of any of a) to c).

5. Use of one or more nucleic acid molecules of any of embodiments 1 or 2 in the detection of the genus *Cronobacter*.

Preferably a pair of primer is employed, most preferably SEQ ID NOs: 2 and 3, optionally plus one or more probes, wherein most preferably the probes are selected from SEQ ID Nos 4-7 and/or 8-9. For all of these SEQ ID NOs respective variants are contemplated.

The nucleic acids used in embodiment 5 may be part of a kit suitable for the detection of the genus *Cronobacter*.

6. A combination of two or more nucleic acids of any of embodiments 1 to 2, optionally in combination with one or more nucleic acids of any of embodiments 3 to 4. Suitable combinations include
   a) a pair of primers of embodiments 1 or 2;
   b) preferably a pair of primers of embodiments 1 or 2 plus 1 or 2 probes of embodiment 2;
   c) more preferably a pair of primers of embodiments 1 or 2 plus 1 or 2 probes of embodiment 2 plus 1 or 2 probes of embodiment 3 or 4; or
   d) more preferably a pair of primers of embodiment 1 or 2 plus probes of embodiments 3 or 4.

Optionally the combinations above may be provided in combination with two or more nucleic acids suitable as primer or probe in the detection of the genus Enterobacteriaceae. These Sequences may be those contemplated in European Patent application EP1254254—NUCLEIC ACID MOLECULES FOR DETECTING BACTERIA AND PHYLOGENETIC UNITS OF BACTERIA or variants of the respective sequences or SEQ ID NOs, which variants are defined as in this patent application.

The combinations of nucleic acids of embodiment 6 may be part of a kit.

7. Use of one or more nucleic acid molecules of any of embodiments 1 or 2 together with one or more nucleic acids of any of embodiments 3 to 4 in the detection of the genus *Cronobacter* and the discrimination of *Cronobacter turicensis* against other species.

8. A method for amplifying bacterial DNA of the taxonomic unit genus *Cronobacter* or for detecting *Cronobacter* in a sample, using primers, in which
   a) in a first amplification step the DNA of the genus *Cronobacter* is amplified with conserved primers of the present invention,
   b) optionally, in at least one further amplification step the DNA of the family Enterobacteriaceae is amplified with conserved primers;
   c) optionally, in a further detection step, the DNA fragments obtained by amplification step a) or b), which are specific for the genus *Cronobacter* or species within said genus or the family Enterobacteriaceae, respectively, are detected by means of probes,
wherein the primers used in the first amplification step comprise a nucleic acid as defined in any of embodiments 1 or 2;
wherein optionally the probes used in step c) comprise a nucleic acid as defined in any of embodiments 1 or 2 which are specific for the genus *Cronobacter*,
wherein optionally the probes used in step c) comprise a nucleic acid as defined in any of embodiments 3 or 4 which are specific for the species within the genus *Cronobacter*, and
wherein the primers and probes for the amplification and/or detection of the family Enterobacteriaceae are as set forth under embodiment 6.

9. The method of embodiment 8, wherein
   d) in a further detection step, the DNA fragments obtained by amplification step a) which are specific for the genus *Cronobacter* are detected by means of probes,
wherein the probes used in step b) comprise a nucleic acid as defined in any of embodiments 1 or 2 which are specific for the genus *Cronobacter*.

10. The method of embodiment 8 or 9, wherein
    e) in a further detection step, the DNA fragments obtained by amplification step a) which are specific for the species *Cronobacter turicensis* are detected by means of probes,
wherein the probes used in step c) comprise a nucleic acid as defined in any of embodiments 3 or 4.

11. The method of any of embodiments 8 to 10, wherein
    f) in at least one further amplification step the DNA of the taxonomic unit Enterobacteriaceae is amplified with conserved primers.

12. The method of embodiment 11, wherein
    g) in a further detection step, the DNA fragments obtained by amplification step f) which are specific for Enterobacteriaceae are detected by means of probes.

13. The method of any of embodiments 8 to 12, wherein the process involves a PCR amplification of the nucleic acid to be detected.

14. The method of any of embodiments 8 to 12, wherein the process involves a Southern Blot hybridization.

15. The method of any of embodiments 9 to 14, wherein one or more probes are modified or labelled so that it can generate a signal in analytical detection procedures which are known per se, with the modification selected from (i) radioactive groups, (ii) coloured groups, (iii) fluorescent groups, (iv) groups for immobilization of a solid phase, and (v) groups which allow a direct or indirect reaction, especially using antibodies, antigens, enzymes, and/or substances with affinity to enzymes or enzyme complexes.

16. The method of any of embodiments 8 to 15, including a step
of amplifying an amplification control nucleic acid, which is added during amplification step a).

A suitable probe for detecting the amplification control is SEQ ID NO:22 or a variant thereof.

17. The method of any of embodiment 9 to 13 or 15 to 16 further including a melting curve analysis, wherein the hybridization behavior of one or more particular probes is studied with time and is used to discriminate between different species of a genus.

Preferably a *C. turicensis* subgroup may be discriminated against other *Cronobacter* species.

18. The method of any of embodiments 8 to 13 or 15 to 17, wherein viable *Cronobacter* or other Enterobacteriaceae cells are discriminated against non-viable *Cronobacter* or other Enterobacteriaceae cells, respectively, wherein an intercalator, e.g. EMA or PMA, is employed to inactivate the DNA in non-viable cells.

FIGURES OF THE INVENTION

FIG. 2 shows the Comparison of the 23S-ITS2-5S region of the type strain of *C. sakazakii* (DSM 4485) with sequences of the species *E. helveticus, E. pulveris* and *E. turicensis*.

Figure 5:
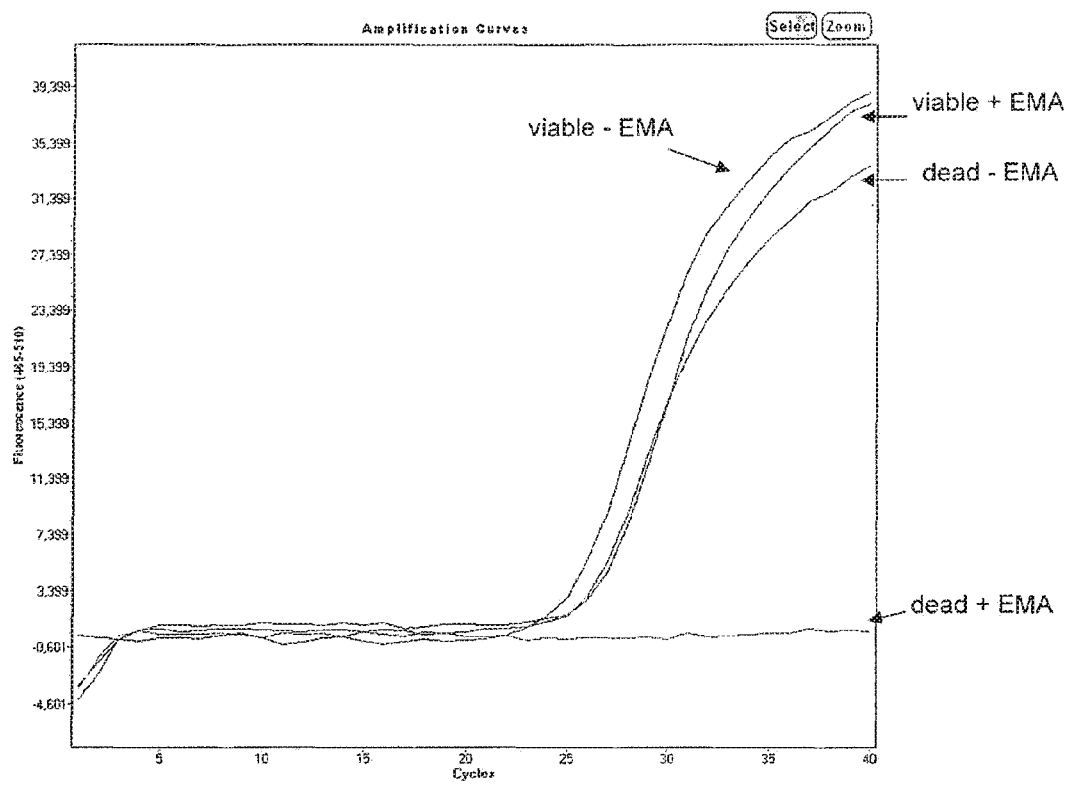

FIG. 5 shows the selective amplification of DNA from viable *Cronobacter* cells after treatment with EMA. Enrichment cultures with $10^6$/ml viable or dead *C. sakazakii* cells were prepared with or without treatment with ethidium monoazide bromide (EMA). The resulting DNA extracts were tested with the multiplex real-time PCR for *Cronobacter* and Enterobacteriaceae detection.

EXAMPLES

Example 1: Comparison of Three Primer Pairs Targeting the Ribosomal Operon Regarding Detection Sensitivity of DNA of *Cronobacter* spp.

Genomic DNA was isolated from pure cultures of the bacteria listed in Table 1 using known standard methods. Dilutions (DNA concentration 100 pg/μl and 1 pg/μl) of these preparations were then added to three different PCR mixes with the following compositions:
Mix A: with primer pair es-16s-for (CAA GTC GAA CGG TAA CAG GG) (SEQ ID NO: 35)/es-16s-rev (GTC CCC CAC TTT GGT CCG) (SEQ ID NO: 36) targeting the 16S rDNA gene published by Malorny & Wagner, 2005 (J. Food Prot. 68: 1623-1627).

Mix B: with primer pair ESFor (ATC TCA AAA MTG ACT GTA AAG TCA CGT T) (SEQ ID NO: 37)/ESRevB (CCG AAR AAG TMT TCG KGC TGC GA) (SEQ ID NO: 38) targeting the region between tRNA-glu- and 23S rDNA-gene published by Derzelle & Dilasser, 2006 (BMC Microbiol. 6: 100).

Mix C: with primer pair SEQ ID NO: 2/SEQ ID NO: 3 targeting the 23S-ITS2-5S region of this invention.

| Component | Final Conc. Mix A | Final Conc. Mix B | Final Conc. Mix C |
|---|---|---|---|
| H$_2$O | — | — | — |
| PCR buffer | 1 x conc. | 1 x conc. | 1 x conc. |
| MgCl$_2$ | 4.5 mM | 3 mM | 3.75 mM |
| dNTP-mix | 200 µM each | 200 µM each | 200 µM each |
| Primer es-16s-for | 400 nM | — | — |
| Primer es-16s-rev | 400 nM | — | — |
| Primer ESFor | — | 500 nM | — |
| Primer ESRevB | — | 500 nM | — |
| SEQ ID NO: 2 | — | — | 600 nM |
| SEQ ID NO: 3[a] | — | — | 600 nM |
| Taq DNA Polymerase | 0.06 U/µl | 0.06 U/µl | 0.06 U/µl |
| Sybr Green ® | 0.25 x conc | 0.25 x conc | 0.25 x conc |
| Sample DNA | Var. | Var. | Var. |

[a]Complement sequence was used

As described by Derzelle & Dilasser the "FastStart Taq Polymerase" (Roche Diagnostics) was used to prevent unspecific amplification. The DNA intercalating fluorescent dye Sybr Green® was added to estimate the PCR efficiency by measuring the CT-values on a real-time PCR instrument.

The PCR was carried out on a LightCycler® 480 instrument (Roche Diagnostics) according to the following protocols:

| Protocol 1 for mix A and C | | |
|---|---|---|
| Initial denaturation | 95° C. | 10 min. |
| Amplification (45 cycles) | 95° C. | 15 s. |
| | 66° C. | 30 s. |
| | 72° C. | 5 s. |
| | 84° C. | 10 s. (fluorescence acquisition) |
| Protocol 2 for mix B and C | | |
| Initial denaturation | 95° C. | 10 min. |
| Amplification (45 cycles) | 95° C. | 15 s. |
| | 60° C. | 10 s. |
| | 72° C. | 25 s. (fluorescence acquisition) |

TABLE 1

Detection sensitivity of primer pair SEQ ID NO 2 and SEQ ID NO 3 (mix C) in comparison to two other primer pairs targeting the ribosomal operon

| | | CP-Value[1] | | | |
|---|---|---|---|---|---|
| Strain | DNA amount | Mix A Protocol 1 | Mix B Protocol 2 | Mix C Protocol 1 | Mix C Protocol 2 |
| C. sakazakii DSM 4485 | 250 pg | 15.5 | 22.1 | 15.9 | 16.3 |
| C. sakazakii DSM 4485 | 2.5 pg | 23.5 | 33.7 | 22.7 | 24.6 |
| C. dublinensis subsp. dublinensis DSM 18705 | 250 pg | 29.4 | 21.8 | 16.7 | 16.9 |
| C. dublinensis subsp. dublinensis DSM 18705 | 2.5 pg | 31.8 | 31.1 | 23.5 | 24.3 |
| C. dublinensis subsp. lactaridi DSM 18707 | 250 pg | 18.8 | 23.1 | 15.7 | 16.1 |
| C. dublinensis subsp. lactaridi DSM 18707 | 2.5 pg | 25.4 | 33.4 | 22.6 | 23.8 |
| C. malonaticus DSM 18702 | 250 pg | 16.3 | 24.0 | 16.5 | 17.8 |
| C. malonaticus DSM 18702 | 2.5 pg | 23.5 | 34.4 | 23.5 | 24.6 |
| C. muytjensii ATCC 51329 | 250 pg | 34.5 | 23.7 | 15.7 | 16.0 |
| C. muytjensii ATCC 51329 | 2.5 pg | negative | 33.8 | 22.5 | 22.9 |
| C. turicensis DSM 18703 | 250 pg | 20.8 | 32.0 | 15.6 | 16.2 |
| C. turicensis DSM 18703 | 2.5 pg | 25.3 | 35.2 | 22.5 | 22.7 |

[1]CP-Value: The crossing point is calculated by the LightCycler Software as the cycle at which PCR amplification begins its detectable exponential phase Example 2: Discrimination of *C. turicensis* from Other *Cronobacter* Spp. by Melting Curve Analysis Genomic DNA was isolated from pure cultures of the bacteria listed in FIG. 2 using known standard methods. The DNA of these preparations was then added to the PCR mix with the following composition (final volume 20 Nl):

| Component | final Concentration |
|---|---|
| H$_2$O | — |
| PCR buffer | 1 x conc. |
| MgCl$_2$ | 3.75 mM |
| dNTP-mix | 200 µM each |
| SEQ ID NO: 2 | 1 µM |
| SEQ ID NO: 3[a] | 300 nM |
| SEQ ID NO: 4-7[b] | 45 nM each |
| SEQ ID NO: 8-9[c] | 100 nM each |
| Taq DNA Polymerase | 0.06 U/µl |
| Sample DNA | 125 fg/µl |

Figure 2:
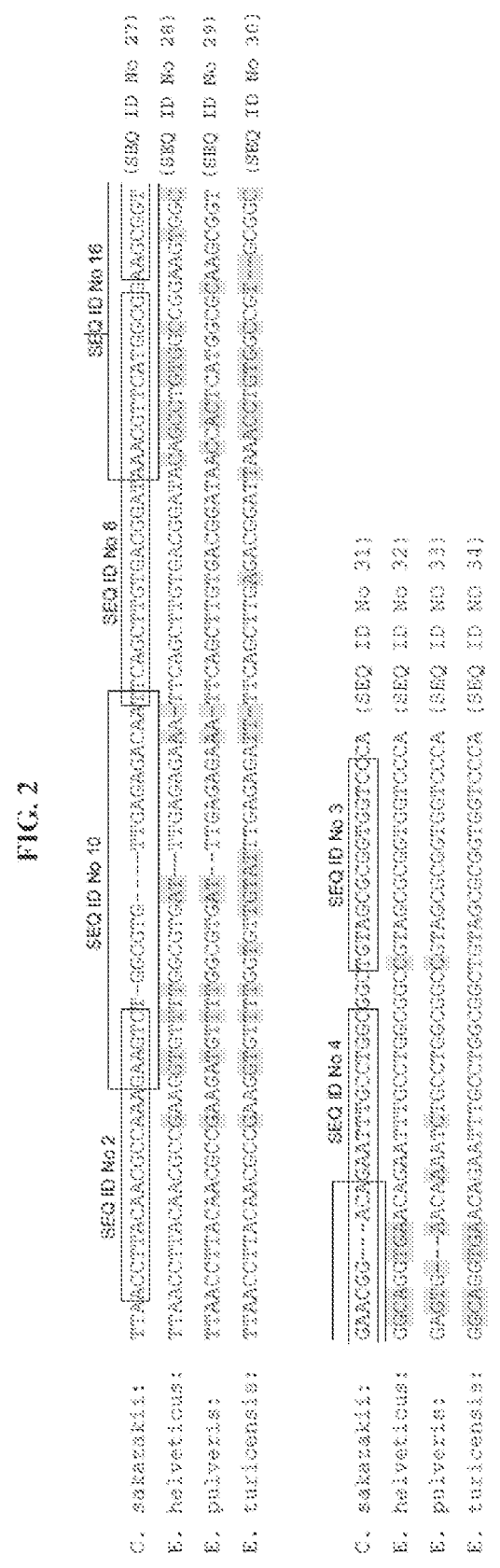

[a]Complement sequence
[b]3'-labeled with fluorescein, complement sequence
[c]5'-labeled with Cy5, complement sequence FIG. 2 shows the Comparison of the 23S-ITS2-5S region of the type strain of *C. sakazakii* (DSM 4485) with sequences of the species *E. helveticus*, *E. pulveris* and *E. turicensis*.

The PCR was carried out on a LightCycler® 2.0 instrument (Roche Diagnostics) according to the following protocol:

| | | |
|---|---|---|
| Initial denaturation | 95° C. | 10 min. |
| Amplification (45 cycles) | 95° C. | 0 s. |
| | 59° C. | 30 s. |
| | 72° C. | 5 s. |
| Melting curve analysis (1 cycle) | 95° C. | 0 s. |
| | 40° C. | 45 s.     ⎫ |
| | 75° C. | 0 s.     ⎬ ramp rate 0.1°/s |
| Cooling | 40° C. | 30 s. |

Figure 1:
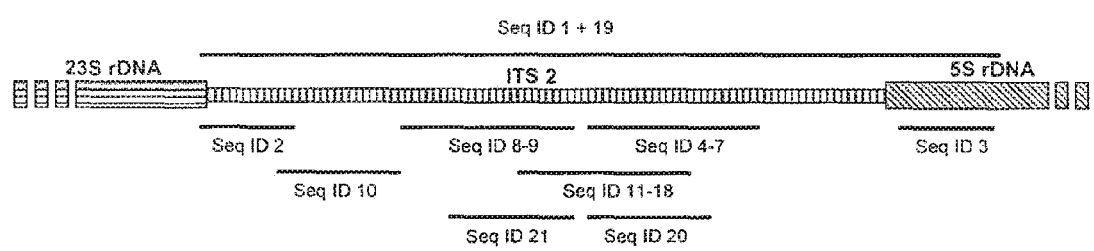
FIG. 1 shows the DNA region as well as the hybridization positions of the oligonucleotides of this invention.
Figure 3:
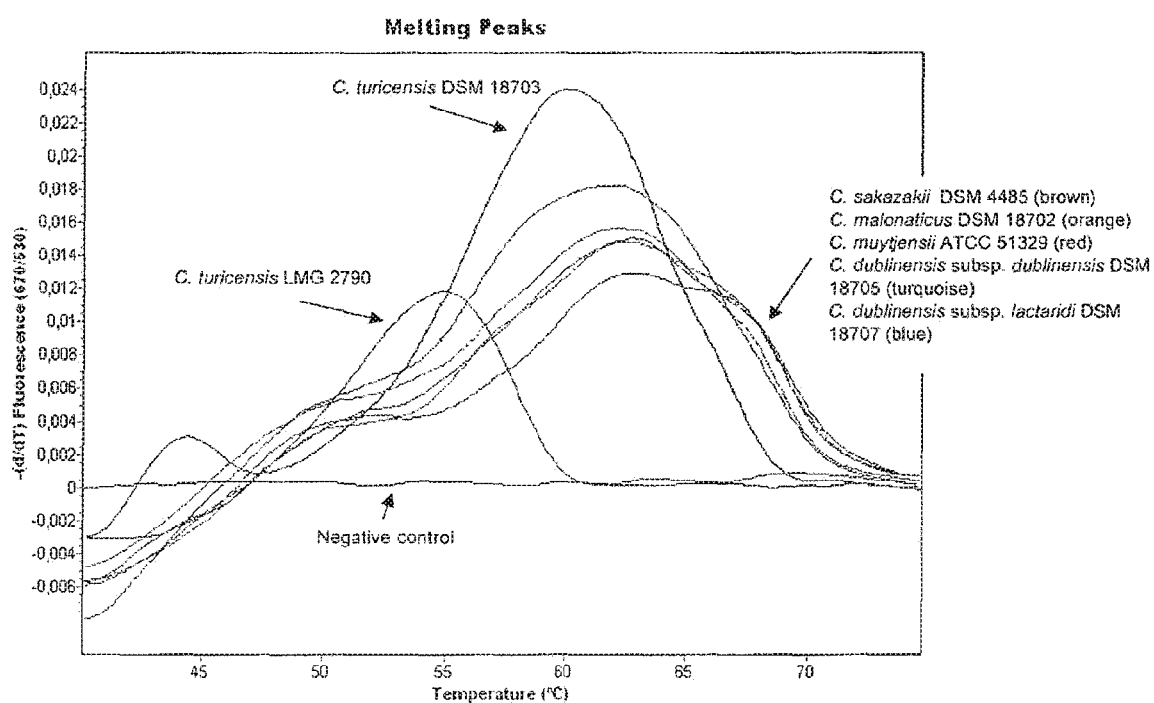
FIG. 3 shows a melting curve analysis for differentiation of *C. turicensis* from other *Cronobacter* spp FIGS. 4A and 4B respectively show shows the simultaneous detection of Enterobacteriaceae and *Cronobacter* spp. by probe-based multiplex real-time PCR.

The melting curve analysis for differentiation of *C. turicensis* from other *Cronobacter* spp is shown in FIG. 3. Coupled to fluorescent molecules oligonucleotides of SEQ ID NO: 4-7 and SEQ ID NO: 8-9 which hybridise adjacently enable the differentiation of *C. turicensis* from other *Cronobacter* species. In addition it is possible to discriminate between different strains of *C. turicensis*.

Example 3: Specific Detection of a Subgroup of *C. turicensis*

Genomic DNA was isolated from pure cultures of the bacteria listed in Table 2 using known standard methods. The DNA of these preparations was then added to the PCR mix with the following composition (final volume 20 µl):

| Component | Final Concentration |
|---|---|
| H$_2$O | — |
| PCR buffer | 1 x conc. |
| MgCl$_2$ | 3.75 mM |
| dNTP-mix | 200 µM each |
| SEQ ID NO: 2 | 600 nM |
| SEQ ID NO: 3[a)] | 600 nM |
| SEQ ID NO: 20[b)] | 180 nM |
| SEQ ID NO: 21[c)] | 200 nM |
| Taq DNA Polymerase | 0.06 U/µl |
| Sample DNA | 125 fg/µl |

[a)]Complement sequence
[b)]3'-labeled with fluorescein, complement sequence
[c)]5'-labeled with Cy5, complement sequence The PCR was carried out on a LightCycler® 2.0 instrument (Roche Diagnostics) according to the following protocol:

| | | |
|---|---|---|
| Initial denaturation | 95° C. | 10 min. |
| Amplification (45 cycles) | 95° C. | 0 s. |
| | 59° C. | 30 s. (fluorescence acquisition) |
| | 72° C. | 5 s. |
| Cooling | 40° C. | 30 s. |

The results of the real-time PCR using the oligonucleotides SEQ ID NO: 20 and SEQ ID NO: 21 as probes are shown in table 2. Only the two *C. turicensis* strains LMG 2790 and E609 were detected.

TABLE 2

Specific PCR detection of a *C. turicensis* subgroup using SEQ ID NO 2, 3, 20 and 21

| Species | Strain | PCR result |
|---|---|---|
| *C. turicensis* | LMG 2790 | + |
| *C. turicensis* | E609 | + |
| *C. turicensis* | DSM 18703 | − |
| *C. turicensis* | BCD 15786 | − |
| *C. dublinensis* subsp. *dublinensis* | DSM 18705 | − |

TABLE 2-continued

Specific PCR detection of a *C. turicensis* subgroup using SEQ ID NO 2, 3, 20 and 21

| Species | Strain | PCR result |
|---|---|---|
| *C. dublinensis* subsp. *lactaridi* | DSM 18707 | − |
| *C. malonaticus* | DSM 18702 | − |
| *C. muytjensii* | ATCC 51329 | − |
| *C. sakazakii* | DSM 4485 | − |
| *C. genomospecies* 1 | NCTC 9529 | − |

Example 4: Detection of *Cronobacter* Spp. by Probe-Based Real-Time PCR

Genomic DNA was isolated from pure cultures of the bacteria listed in Table 3 using known standard methods. The DNA of these preparations (concentration in the area of approx. 10 ng-100 pg) as well as the amplification control DNA were then added to the PCR mix with the following composition (final volume 20 µl):

| Component | final Concentration |
|---|---|
| H$_2$O | — |
| PCR buffer | 1 x conc. |
| MgCl$_2$ | 3.75 mM |
| dNTP-mix | 200 µM each |
| SEQ ID NO: 2 | 600 nM |
| SEQ ID NO: 3[a)] | 600 nM |
| SEQ ID NO: 4-7[b)] | 45 nM each |
| SEQ ID NO: 20[b)] | 180 nM |
| SEQ ID NO: 8-9[c)] | 100 nM each |
| SEQ ID NO: 21[c)] | 200 nM |
| SEQ ID NO: 22[d)] | 200 nM |
| Taq DNA Polymerase | 0.06 U/µl |
| Control DNA | 0.25 fg/µl |
| Sample DNA | var. |

[a)]Complement sequence
[b)]3'-labeled with fluorescein, complement sequence
[c)]5'-labeled with Cy5, complement sequence
[d)]5'-labeled with LC-Red® 610

The PCR was carried out on a LightCycler® 2.0 instrument (Roche Diagnostics) according to the following protocol:

| | | |
|---|---|---|
| Initial denaturation | 95° C. | 10 min. |
| Amplification (45 cycles) | 95° C. | 0 s. |
| | 59° C. | 30 s. (fluorescence acquisition) |
| | 72° C. | 5 s. |
| Cooling | 40° C. | 30 s. |

Amplification of *Cronobacter* spp. DNA was detected in channel 670/back 530. In cases of a negative result amplification of the control DNA should be visible in channel 610/back 530. The results of the probe-based real-time PCR are shown in table 3. All tested *Cronobacter* strains comprising all species and subspecies as well as C. genomospecies 1 were detected. In contrast, none of the tested bacterial strains not belonging to this genus was registered with this system.

The amplification control was detected in channel 610/back 530 for all samples with a negative result for *Cronobacter* DNA. The quality of these non-*Cronobacter* DNA samples was checked with consensus PCR system specific for all eubacteria targeting the 16S rDNA (Barry et al., 1990, Biotechnology 8: 233-236).

TABLE 3

Specific PCR detection of the genus *Cronobacter* using SEQ ID NO 2, 3, 4-7, 8-9, 20 and 21

| Species | Strain[1] | PCR result |
|---|---|---|
| *Cronobacter dublinensis* subsp. *dublinensis* | DSM 18705 | + |
| *Cronobacter dublinensis* subsp. *lactaridi* | DSM 18707 | + |
| *Cronobacter dublinensis* subsp. | NCTC 9844 | + |
| *Cronobacter malonaticus* | DSM 18702 | + |
| *Cronobacter muytjensii* | ATCC 51329 | + |
| *Cronobacter sakazakii* | DSM 4485 | + |
| *Cronobacter turicensis* | DSM 18703 | + |
| *Cronobacter turicensis* | LMG 2790 | + |
| *Cronobacter turicensis* | E609 | + |
| *Cronobacter turicensis* | BCD 15786 | + |
| *Cronobacter* genomospecies 1 | NCTC 9529 | + |
| *Enterobacter sakazakii* | BCD 15300 | + |
| *Enterobacter sakazakii* | BCD 15301 | + |
| *Enterobacter sakazakii* | BCD 15361 | + |
| *Enterobacter sakazakii* | BCD 15381 | + |
| *Enterobacter sakazakii* | BCD 15410 | + |
| *Enterobacter sakazakii* | BCD 15428 | + |
| *Enterobacter sakazakii* | BCD 15429 | + |
| *Enterobacter sakazakii* | BCD 15430 | + |
| *Enterobacter sakazakii* | BCD 15431 | + |
| *Enterobacter sakazakii* | BCD 15432 | + |
| *Enterobacter sakazakii* | BCD 15433 | + |
| *Enterobacter sakazakii* | BCD 15434 | + |
| *Enterobacter sakazakii* | BCD 15435 | + |
| *Enterobacter sakazakii* | BCD 15436 | + |
| *Enterobacter sakazakii* | BCD 15437 | + |
| *Enterobacter sakazakii* | BCD 15438 | + |
| *Enterobacter sakazakii* | BCD 15439 | + |
| *Enterobacter sakazakii* | BCD 15440 | + |
| *Enterobacter sakazakii* | BCD 15441 | + |
| *Enterobacter sakazakii* | BCD 15442 | + |
| *Enterobacter sakazakii* | BCD 15443 | + |
| *Enterobacter sakazakii* | BCD 15444 | + |
| *Enterobacter sakazakii* | BCD 15445 | + |
| *Enterobacter sakazakii* | BCD 15446 | + |
| *Enterobacter sakazakii* | BCD 15447 | + |
| *Enterobacter sakazakii* | BCD 15448 | + |
| *Enterobacter sakazakii* | BCD 15449 | + |
| *Enterobacter sakazakii* | BCD 15450 | + |
| *Enterobacter sakazakii* | BCD 15451 | + |
| *Enterobacter sakazakii* | BCD 15452 | + |
| *Enterobacter sakazakii* | BCD 15459 | + |
| *Enterobacter sakazakii* | BCD 15460 | + |
| *Enterobacter sakazakii* | BCD 15461 | + |
| *Enterobacter sakazakii* | BCD 15462 | + |
| *Enterobacter sakazakii* | BCD 15463 | + |
| *Enterobacter sakazakii* | BCD 15464 | + |
| *Enterobacter sakazakii* | BCD 15469 | + |
| *Enterobacter sakazakii* | BCD 15470 | + |
| *Enterobacter sakazakii* | BCD 15471 | + |
| *Enterobacter sakazakii* | BCD 15472 | + |
| *Enterobacter sakazakii* | BCD 15473 | + |
| *Enterobacter sakazakii* | BCD 15474 | + |
| *Enterobacter sakazakii* | BCD 15475 | + |
| *Enterobacter sakazakii* | BCD 15476 | + |
| *Enterobacter sakazakii* | BCD 15477 | + |
| *Enterobacter sakazakii* | BCD 15478 | + |
| *Enterobacter sakazakii* | BCD 15488 | + |
| *Enterobacter sakazakii* | BCD 15489 | + |
| *Enterobacter sakazakii* | BCD 15490 | + |
| *Enterobacter sakazakii* | BCD 15492 | + |
| *Enterobacter sakazakii* | BCD 15495 | + |
| *Enterobacter sakazakii* | BCD 15497 | + |
| *Enterobacter sakazakii* | BCD 15498 | + |
| *Enterobacter sakazakii* | BCD 15499 | + |
| *Enterobacter sakazakii* | BCD 15500 | + |
| *Enterobacter sakazakii* | BCD 15501 | + |
| *Budvicia aquatica* | DSM 5075 | − |
| *Buttiauxella agrestis* | DSM 4586 | − |
| *Cedecea davisae* | DSM 4568 | − |
| *Citrobacter amalonaticus* | DSM 4593 | − |
| *Citrobacter freundii* | BCD 4696 | − |
| *Citrobacter koseri* | DSM 4595 | − |
| *Edwardsiella tarda* | DSM 30052 | − |
| *Enterobacter aerogenes* | DSM 30053 | − |
| *Enterobacter amnigenus* | DSM 4486 | − |
| *Enterobacter cancerogenus* | CCM 2421 | − |
| *Enterobacter cloacae* | DSM 30054 | − |
| *Enterobacter cowanii* | CCM 7015 | − |
| *Enterobacter gergoviae* | BCD 674 | − |
| *Enterobacter helveticus* | DSM 18396 | − |
| *Enterbacter hormaechei* | DSM 12409 | − |
| *Enterobacter pulveris* | DSM 19144 | − |
| *Enterobacter pyrinus* | DSM 12410 | − |
| *Enterobacter turicensis* | DSM 18397 | − |
| *Erwinia carotovora* | DSM 30168 | − |
| *Erwinia crysanthemi* | DSM 4610 | − |
| *Escherichia coli* | DSM 30083 | − |
| *Escherichia hermannii* | DSM 4560 | − |
| *Escherichia vulneris* | DSM 4564 | − |
| *Hafnia alvei* | DSM 30163 | − |
| *Klebsiella oxytoca* | DSM 5175 | − |
| *Klebsiella pneumoniae* | DSM 30102 | − |
| *Kluyvera ascorbata* | DSM 4611 | − |
| *Kluyvera cryocrescens* | DSM 4588 | − |
| *Leclercia adecarboxylata* | DSM 5077 | − |
| *Morganella (Proteus) morganii* | DSM 30164 | − |
| *Pantoea agglomerans* | DSM 3493 | − |
| *Pantoea ananatis* | DSM 30070 | − |
| *Pantoea dispersa* | DSM 30073 | − |
| *Proteus hauseri* | DSM 30118 | − |
| *Proteus mirabilis* | DSM 788 | − |
| *Providencia alcalifaciens* | DSM 30120 | − |
| *Providencia stuartii* | DSM 4539 | − |
| *Rahnella aquatilis* | DSM 4594 | − |
| *Raoultella (Klebsiella) planticola* | DSM 4617 | − |
| *Raoultella (Klebsiella) terrigena* | DSM 2687 | − |
| *Salmonella Abony* | DSM 4224 | − |
| *Salmonella bongori* | BCD 14407 | − |
| *Serratia ficaria* | DSM 4569 | − |
| *Serratia marcescens* | DSM 1636 | − |
| *Serratia proteamaculans* | DSM 4487 | − |
| *Serratia rubidaea* | DSM 4480 | − |
| *Shigella boydii* | DSM 7532 | − |
| *Yersinia aldovae* | ATCC 35236 | − |
| *Yersinia enterocolitica* | DSM 4780 | − |
| *Yersinia frederiksenii* | ATCC 33641 | − |

For all negative tested strains was the amplification control positive.
[1]Abbreviations stands for the following culture collections:
ATCC: American Type Culture Collection, Manassas, USA
BCD: BIOTECON Diagnostics culture collection, Potsdam, Germany
CCM: Czech Collection of Microorganisms, Brno, Czech Republic
DSM: German Collection of Microorganisms and Cell Cultures, Braunschweig, Germany
LMG: BCCM/LMG Bacteria Collection, Gent, Belgium
NCTC: National Collection of Type Cultures, Salisbury, UK

Example 5: Simultaneous Detection of *Cronobacter* Spp. and Enterobacteriaceae by Probe-Based Multiplex Real-Time PCR Genomic DNA was isolated from pure cultures of the bacteria listed in FIG. 3 using known standard methods. The DNA of these preparations (concentration approx. 5-50 ng) as well as the amplification control DNA was then added to the multiplex PCR mix with the following composition (final volume 25 µl):

| Component | Final Concentration |
|---|---|
| H$_2$O | — |
| PCR buffer | 1 × conc. |
| MgCl$_2$ | 3.75 mM |
| dNTP-mix | 200 µM each |
| SEQ ID NO: 2 | 600 nM |

-continued

| Component | Final Concentration |
|---|---|
| SEQ ID NO: 3[a)] | 600 nM |
| SEQ ID NO: 8-9[b)] | 125 nM each |
| SEQ ID NO: 21[b)] | 250 nM |
| Enterobacteriaceae forward-primer | 600 nM |
| Enterobacteriaceae reverse-primer | 600 nM |
| Enterobacteriaceae probes 1-4[c)] | 150 nM each |
| Taq DNA Polymerase | 0.06 U/µl |
| Control DNA | 0.25 fg/µl |
| Sample DNA | var. |

[a)]Complement sequence
[b)]5'-labeled with FAM, 3'-labeled with a quencher, complement sequence
[c)]5'-labeled with HEX, 3'-labeled with a quencher The Enterobacteriaceae forward-primer is equivalent to SEQ ID NO 2 (TTC GGG TTG TCATGC CAA TG), the Enterobacteriaceae reverse-primer to the complement sequence of SEQ ID NO 78 (ACC CGT GAG GCT AAC CT TAC AAC ACC GAA) of the invention WO 01/023606, and the Enterobacteriaceae probes 1-4 are equivalent to SEQ ID NO 3 (CTG AAA GCA TCT AAG CGC GAA ACT TG), SEQ ID NO 4 (CTG AAA GCA TCT AAG CGG GAA ACT TG), SEQ ID NO 5 (CTG AAA GCA TCT AAG CAC GAA CTT G) and SEQ ID NO 6 (CTG AAA GCA TCT AAG CAC GAA ACT TG) of the invention WO 01/023606.

The PCR was carried out on a LightCycler® 480 instrument (Roche Diagnostics) according to the following protocols:

| Initial denaturation | 95° C. | 5 min. |
|---|---|---|
| Amplification (40 cycles) | 95° C. | 10 s. |
| | 65° C.-61° C. | 70 s. (fluorescence acquisition) |
| | step down each cycle by 0.1° C. | |

Figure 4:
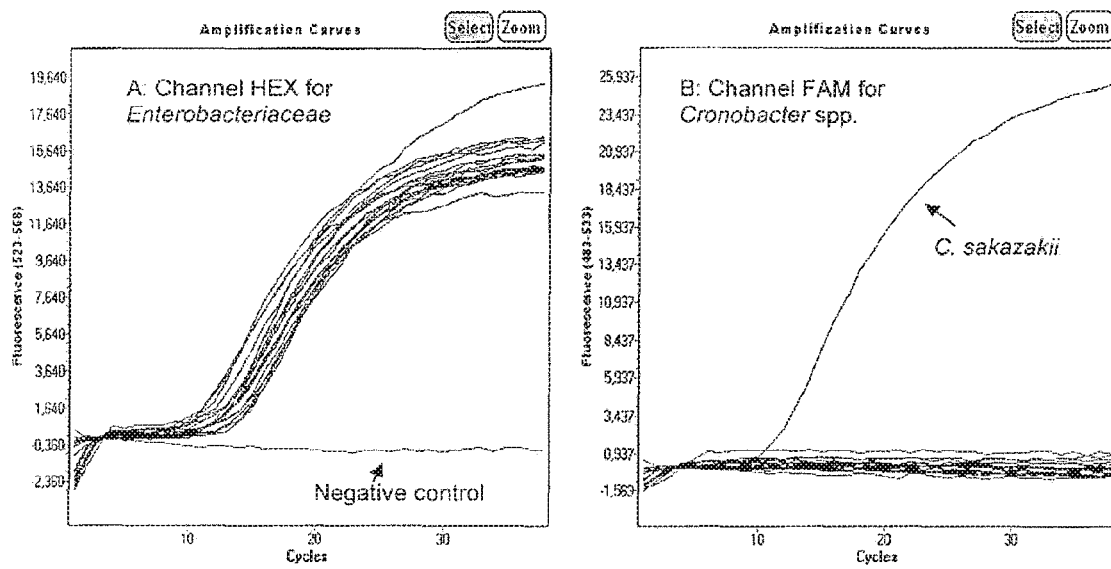

The results of the probe-based multiplex real-time PCR are shown in FIG. 4, which shows the simultaneous detection of *Cronobacter* spp. and Enterobacteriaceae by probe-based multiplex real-time PCR. The specific detection of *Cronobacter* DNA occurred in the FAM-whereas the DNA amplification of the complete Enterobacteriaceae family could be detected in the HEX-channel.

Example 6: Selective Amplification of DNA from Viable *Cronobacter* Cells

An according to ISO/TS 22964 pre-enriched sample of infant formula was subcultivated in buffered peptone water (BPW). This subculture were inoculated to $10^6$ dead *C. sakazakii* cells per ml. Inactivation was done by incubation of a *C. sakazakii* culture with $5\times10^6$/ml for 10 min at 70° C. (inactivation checked by plating). As controls additional samples were inoculated with viable *C. sakazakii* cells.

For selective inactivation of DNA from dead cells 100 µl of each sample were mixed with 300 µl of a solution containing 20 µg/ml ethidium bromide monoazide (EMA). After incubation for 5 minutes in dark, the samples were placed on ice, exposed for 5 minutes to a 500 W halogen light bulb in approx. 15-20 cm distance. Afterwards the mixtures were centrifuged (5 min. at 10 000×g) and the supernatant discarded. DNA isolation was performed by resuspension of the cell pellet in 200 µl lysis solution containing Chelex x-100 and incubation at 95-100° C. for 10 minutes. As controls the DNA from 100 µl of all spiked samples was isolated without a treatment with EMA.

PCR mix and protocol were the same as in example 5. The results of this experiment are shown in FIG. 5.

As shown in FIG. 5 the addition of DNA from dead *Cronobacter* cells without a treatment with EMA to the *Cronobacter* specific PCR system results in clearly visible fluorescence curves, whereas in the treated samples no amplification is detectable. On viable cells the PCR detection sensitivity is only slightly reduced by this EMA-procedure. Therefore the PCR-based method of this invention could be combined with the EMA-technique and enables a sensitive detection of only viable *Cronobacter* cells.

The invention claimed is:

1. A method of amplifying DNA, comprising,
   providing a sample comprising bacteria,
   amplifying DNA from the bacteria with primers in an amplification step, wherein the primers used in the amplification step comprise a first primer comprising SEQ ID NO:2 or a variant thereof, together with a second primer comprising the complement of SEQ ID NO:3 or a variant thereof,
   wherein the variant of the first primer is a sequence which is identical to SEQ ID NO:2 other than the substitution of one nucleotide base within SEQ ID NO:2 with a different base and the variant of the second primer is a sequence which is identical to the complement of SEQ ID NO:3 other than the substitution of one nucleotide base within the complement of SEQ ID NO:3 with a different nucleotide base,
   wherein the sample comprises *Cronobacter sakazakii* strain DSM 4485 and *Enterobacter turicensis* strain DSM 18397, and wherein the primers amplify DNA from *Cronobacter sakazakii* strain DSM 4485, but do not amplify DNA from *Enterobacter turicensis* strain DSM 18397.

2. The method of claim 1, wherein the sample further comprises *Enterobacter helveticus* strain DSM 18396, and wherein the primers also do not amplify DNA from *Enterobacter helveticus* strain DSM 183966.

3. The method of claim 2, wherein the sample further comprises *Enterobacter pulveris* strain DSM 19144, and wherein the primers also do not amplify DNA from *Enterobacter pulveris* strain DSM 19144.

* * * * *